United States Patent [19]

Yoon

[11] Patent Number: 5,676,657
[45] Date of Patent: Oct. 14, 1997

[54] ENDOSCOPIC PORTAL HAVING MULTILUMINAL TRUMPET VALVE

[76] Inventor: InBae Yoon, 2101 Highland Ridge Dr., Phoenix, Md. 21131

[21] Appl. No.: 618,326

[22] Filed: Mar. 19, 1996

Related U.S. Application Data

[63] Continuation-in-part of Ser. No. 369,240, Jan. 6, 1995, and a continuation of Ser. No. 557,869, Jul. 26, 1990, Pat. No. 5,395,342.

[51] Int. Cl.$^6$ .................................................. A61M 5/178
[52] U.S. Cl. .......................... 604/167; 604/165; 604/247
[58] Field of Search ................................... 604/164, 167, 604/256, 246, 247, 248, 249

[56] References Cited

U.S. PATENT DOCUMENTS

| | | | |
|---|---|---|---|
| 3,895,632 | 7/1975 | Plowiecki | 604/169 |
| 4,126,133 | 11/1978 | Schwartz | 604/169 |
| 4,593,717 | 6/1986 | Levasseur | 604/248 |
| 5,211,633 | 5/1993 | Stouder, Jr. | 604/167 |
| 5,275,563 | 1/1994 | Crainich | 604/164 |
| 5,300,036 | 4/1994 | Mueller | 604/167 |
| 5,350,362 | 9/1994 | Stouder, Jr. | 604/167 |
| 5,356,394 | 10/1994 | Farley | 604/246 |
| 5,512,053 | 4/1996 | Pearson | 604/164 |

Primary Examiner—Sam Rimell
Assistant Examiner—Luke J. Yeh

[57] ABSTRACT

An endoscopic portal for establishing communication with a body cavity for the introduction of instruments therethrough includes a sleeve for providing a passage through a cavity wall and a valve biased to a normal closed position preventing the passage of instruments and fluids through the sleeve. The sleeve includes a distal end for being disposed in a body cavity, a proximal end for being disposed externally of the body cavity and a lumen between the distal and proximal ends. The valve includes a cylindrical valve body extending in a transverse direction across the lumen and having a plurality of diametric valve passages therethrough of different cross sectional sizes. The valve body is biased to the normal closed position wherein the valve body blocks communication through the lumen and wherein the valve passages are not disposed within the lumen. The valve body is movable axially from the normal closed position to position the valve passages within the lumen, and the valve body is rotatable about an axis transverse to the longitudinal axis of the sleeve to align a selected one of the valve passages axially with the lumen such that an instrument having a cross sectional size corresponding to the cross sectional size of the selected valve passage can be introduced through the lumen to extend through the valve body in sealing relation.

20 Claims, 2 Drawing Sheets

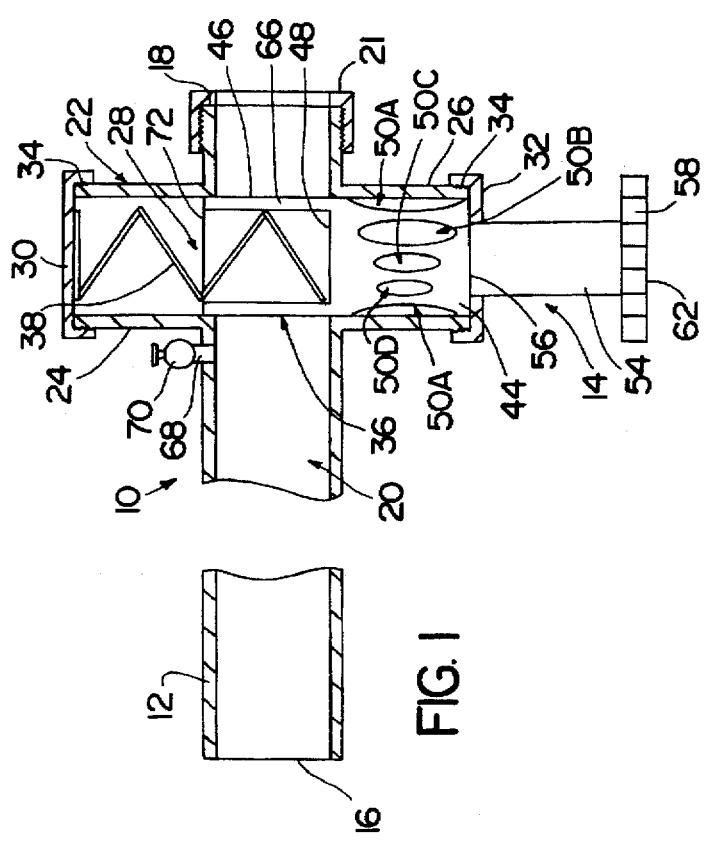

ENDOSCOPIC PORTAL HAVING MULTILUMINAL TRUMPET VALVE

CROSS-REFERENCE TO RELATED APPLICATIONS

This application is a continuation-in-part of pending application Ser. No. 08/369,240 filed Jan. 6, 1995 which is a continuation of Ser. No. 07/557,869 filed Jul. 26, 1990, now U.S. Pat. No. 5,395,342, the disclosures of which are incorporated herein by reference.

BACKGROUND OF THE INVENTION

1. Field of the Invention

The present invention pertains to endoscopic portals providing a passage through a cavity wall and, more particularly, to an endoscopic portal having a valve providing a variable size passage to prevent fluid flow through the endoscopic portal while allowing instruments of various sizes to be selectively introduced therethrough.

2. Brief Description of the Prior Art

In endoscopic procedures, a portal, such as a sleeve or cannula or other structure forming a passage, is normally disposed in a body cavity wall such that a distal end of the portal is positioned within the body cavity and a proximal end of the portal is disposed externally of the body cavity to provide a passage establishing communication with an internal site from externally of the body cavity. The portal is typically disposed in the cavity wall with the use of a penetrating member, such as a trocar, obturator or needle, disposed in the portal and having a distal tip for penetrating the cavity wall. Upon entry of the distal end of the portal in the body cavity, the penetrating member is withdrawn leaving the portal in situ to provide a passage through the cavity wall establishing communication with an internal operative site from externally of the cavity. Typically, various instruments are introduced at the internal operative site through the passage defined by the portal in order to perform diagnostic and/or surgical procedures, with the instruments many times having varying sizes in cross section. It is important in endoscopic procedures to prevent undesired fluid flow to and from the internal site; and, accordingly, the portal must be sealed prior to and subsequent to the introduction of instruments and while the instruments are in place. In particular, fluids such as gaseous phase carbon dioxide or nitrous oxide are normally introduced in the body for insufflation as part of the endoscopic procedure, and the escape of such gases through the portal should be prevented.

Many endoscopic portals have valves that close when the penetrating member is removed from the portal to prevent the flow of fluids to and from the body cavity. Many valves utilized in endoscopic portals include a valve passage having a fixed size. Instruments larger in size than the fixed size of the valve passage cannot be introduced through the valve passage into the portal; and, when instruments smaller in size than the fixed size of the valve passage are introduced, fluid can flow past the smaller size instruments. Such endoscopic portals suffer from the disadvantages of allowing the passage or leakage of fluids when instruments smaller in size than the fixed size of the valve passage are introduced therethrough or of limiting the instruments to be used in a procedure to a single size. Accordingly, such endoscopic portals can be effectively used with only a single size penetrating member; however, the size of the penetrating member to be optimally utilized varies depending upon the procedure and the type of body cavity to be penetrated.

SUMMARY OF THE INVENTION

Accordingly, it is a primary object of the present invention to overcome the aforementioned disadvantages of the prior art by utilizing a multiluminal trumpet valve in an endoscopic portal to provide a variable size passage therethrough to engage instruments of various sizes in sealing relation.

Another object of the present invention is to define multiple lumens or valve passages of diverse cross sectional sizes in a trumpet valve for an endoscopic portal to selectively produce a sealing relation with instruments of various sizes.

A further object of the present invention is to normally seal an endoscopic portal utilizing a trumpet valve and to selectively permit instruments of diverse sizes to be introduced through the portal while preventing fluid flow or leakage therethrough.

The present invention has as another object to utilize a valve body that is both axially movable and rotatable to align a selected valve passage of the valve body with the lumen of a sleeve for selectively producing a sealing relation with instruments of various sizes introduced through the valve body and the sleeve.

Some of the advantages of the present invention are that a complete endoscopic procedure can be performed with a single endoscopic portal thereby reducing instrument costs and surgery time, a single endoscopic portal can be used with various sizes and types of instruments including various size penetrating members, the size of the valve housing for the endoscopic portal can be minimized, the overall length of the endoscopic portal can be minimized since the valve housing does not add significantly to the length of the endoscopic portal, the valve can be housed in an extension of the sleeve for economy of structure and manufacturing, and the endoscopic portal can be inexpensively manufactured to be economically disposable for single patient use.

These and other objects, advantages and benefits are realized with the present invention as characterized in an endoscopic portal comprising a sleeve for providing a passage through a cavity wall and a valve biased to a normal closed position blocking a lumen of the sleeve. The sleeve includes a distal end for being disposed in a body cavity, a proximal end for being disposed externally of the body cavity, a lumen between the distal and proximal ends for receiving instruments, and a longitudinal axis. The valve includes a cylindrical valve body extending in a direction transverse to the longitudinal axis of the sleeve and having a lumen blocking portion and a valve passage defining portion including a plurality of diametric valve passages therethrough of different cross sectional sizes. The valve is biased to the closed position wherein the lumen blocking portion is disposed within the lumen of the sleeve to close off or block the lumen to prevent the passage of instruments and fluids therethrough and wherein the valve passage defining portion is disposed externally of the lumen. A bias member biases the valve body to the normal closed position and permits the valve body to be manually moved axially in the transverse direction to position the valve passage defining portion within the lumen. The bias member maintains the valve body in an initial rotational position and permits the valve body to be rotated about an axis transverse or perpendicular to the longitudinal axis of the sleeve to align a selected one of the valve passages axially with the lumen such that an instrument having a cross sectional size corresponding to the cross sectional size of the selected valve passage can be introduced in the lumen to extend through the valve in sealing relation therewith.

Other objects, advantages and benefits of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 1 is a broken, side sectional view of an endoscopic portal according to the present invention showing the valve of the endoscopic portal in the normal closed position.

FIG. 2 is a perspective view of the valve body of the valve for the endoscopic portal.

FIG. 3 is a distal end view of the valve body.

FIG. 4 is a proximal end view of the valve body.

DESCRIPTION OF THE PREFERRED EMBODIMENT

Figure 6:
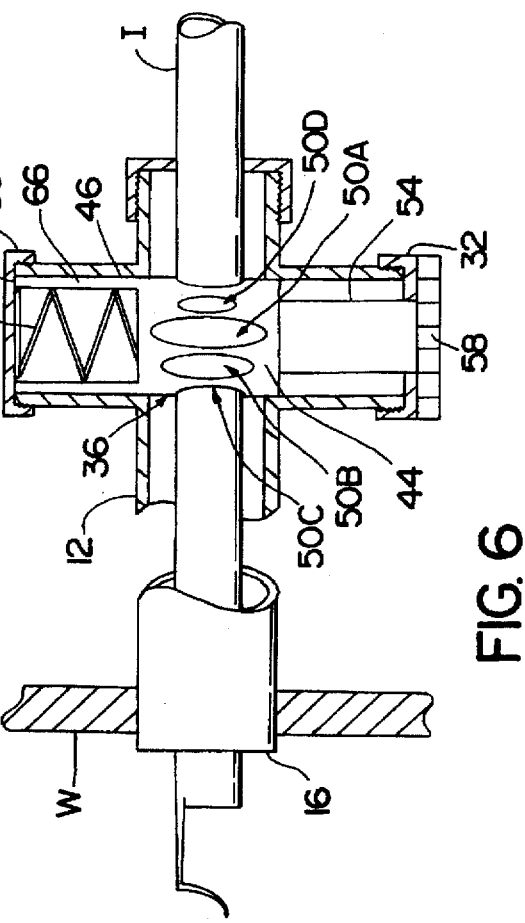
FIG. 6 is a broken, side sectional view of the endoscopic portal showing the valve in a second open position to receive a different size instrument therethrough.

An endoscopic portal 10 according to the present invention is illustrated in FIG. 1 and includes an elongate sleeve 12 and a multiluminal valve 14 for opening and closing a lumen or passage through sleeve 12. Sleeve 12, which, for example, can take the form of a cannula or portal sleeve or other structure providing a passage through a cavity wall, has an open distal end 16 for being disposed at an internal site in a body cavity, an open proximal end 18 for being disposed externally of the cavity and a lumen 20 between the distal and proximal ends. The proximal end 18 of sleeve 12 is externally threaded for releasable engagement with an internally threaded end cap 21 having an opening therein communicating with lumen 20; however, an end cap at the proximal end of the sleeve may not be necessary. The opening in end cap 21 is axially aligned with lumen 20 and has a size corresponding to the cross sectional size of an instrument to be introduced through the endoscopic portal 10 for added stability. When an instrument having a cross sectional size different than the size of the opening in end cap 21 is to be introduced, end cap 21 can be removed and replaced with a different end cap having an opening corresponding in size to the cross sectional size of the instrument to be introduced. The lumen 20 has a cross sectional size to receive instruments of various cross sectional sizes smaller than the lumen cross sectional size.

Sleeve 12 includes a transverse extension 22 between the distal end 16 and the proximal end 18 serving as a valve housing for valve 14. Transverse extension 22 includes cylindrical end members 24 and 26 coaxially aligned with one another and protruding in a transverse direction from sleeve 12 such that the common longitudinal axis of end members 24 and 26 is disposed transverse or perpendicular to a longitudinal axis of sleeve 12. End members 24 and 26 are each hollow or tubular to communicate with the lumen 20 such that a transverse cavity 28 for housing the valve 14 is defined by the hollow interiors of end members 24 and 26, respectively, and the portion of lumen 20 disposed between end members 24 and 26. End members 24 and 26 have open outer ends with end caps 30 and 32 disposed thereon, respectively. End cap 30 is solid to provide an end wall closing off the open outer end of end member 24 while end cap 32 has an opening therein through which a handle of the valve 14 protrudes as described further below. The end caps 30 and 32 can be secured on or to the outer ends of end members 24 and 26, respectively, in many various ways including being releasably secured to the outer ends of the end members with the use of mating threads 34 to facilitate assembly of the valve 14 to the sleeve 12.

Valve 14 is in the nature of a trumpet valve including a valve body 36 and a bias member 38 biasing the valve body 36 to a normal closed position. As best shown in FIGS. 1 and 2, valve body 36 includes a cylindrical member 40 and a handle 42 protruding from cylindrical member 40. Cylindrical member 40 has a valve passage defining section or portion 44 and a lumen blocking section or portion 46 extending from a transverse intermediate wall 48. Lumen blocking portion 46 is hollow or tubular to define a recess therein for receiving bias member 38. Valve passage defining portion 44 is solid with a plurality of diametric valve passages 50 formed therethrough, and the passages 50 are of different cross sectional sizes. Preferably, three or more valve passages 50 are provided in the valve body 36; and, in the case of valve 14, four valve passages 50A, 50B, 50C and 50D having circular cross sectional configurations are formed in valve passage defining section 44. As shown in FIG. 3, longitudinal axes of valve passages 50A, 50B, 50C and 50D intersect one another at a longitudinal axis of valve body 36. Valve passage 50A has the largest cross sectional size, valve passage 50B has the next largest cross sectional size, valve passage 50C has the third largest cross sectional size, and valve passage 50D has the smallest cross sectional size.

Handle 42 includes a cylindrical shaft 54 extending axially from a transverse end wall 56, parallel to intermediate wall 48, and a knob 58 at the free end of shaft 54. Knob 58 is of uniform thickness and has a circular configuration with grooves 60 along the circumference thereof to facilitate grasping. As shown in FIG. 4, an external or outer face or surface 62 of knob 58 carries indicia 64 visually identifying the location and size of valve passages 50. Indicia 64 for each valve passage 50 includes numbers at opposite ends of the valve passage, the numbers identifying the size of the valve passage. As shown, for example, in FIG. 4, the number "10" is disposed closely adjacent the circumference of knob 58 at opposite ends of valve passage 50A to indicate that the diameter of valve passage 50 A is 10 mm. In the same manner, the size of valve passage 50B is indicated as being 7 mm in diameter, the size of valve passage 50C is indicated as being 5 mm in diameter, and the size of valve passage 50D is indicated as being 3 mm in diameter. The indicia for each valve passage are aligned with one another along the longitudinal axis of the valve passage; and, accordingly, the indicia 64 provide a visual indication of the location of the valve passage as well as the size thereof.

Valve body 36 is arranged in the valve housing with cylindrical member 40 closely received in cavity 28 with shaft 54 protruding through the opening in end cap 32. Bias member 38 is in the nature of a helical coil spring 38 disposed in cavity 28 and mounted in compression between end cap 30 and intermediate wall 48 such that the valve body 36 is biased in an axial direction toward end cap 32. With the valve body 36 biased by spring 38, the valve body 36 is in an extended position with end wall 56 in abutment with end cap 32 and knob 58 spaced from end cap 32 by shaft 54. The valve passage defining section 44 is disposed in end member 26 to be laterally offset from or disposed externally or outside of lumen 20 such that the valve passages 50 do not communicate with and are not axially aligned with lumen 20. The lumen blocking section 46 is disposed in lumen 20 such that a solid circumferential wall 66 of the lumen blocking section 46 extends across lumen 20 to close off or block lumen 20 and prevent communication therewith. The circumferential wall 66 extends transversely across the lumen 20 and is in contact with internal surfaces of end members 24 and 26, respectively, due to the valve body being closely received in the cavity 28, to create a fluidic seal preventing fluid flow through the lumen 20. The valve 14, therefore, is biased to a normal closed position with the valve body 36 biased to the extended position to create a seal closing off the lumen 20 to the passage of instruments and fluids.

The ends of spring 38 are connected to end cap 30 and valve body 36, respectively, to position or maintain the valve body 36 in a first or initial rotational position when the valve 14 is in the normal closed position. In the case of valve 14, valve passage 50A is disposed parallel with the lumen 20 when the valve body 36 is in the first or initial rotational position and in the extended position; and, accordingly, with the valve 14 in the normal closed position, the longitudinal axis of valve passage 50A is disposed parallel to and laterally offset from the longitudinal axis of sleeve 12. The remaining valve passages 50B, 50C and 50D are not parallel with lumen 20; and, therefore, the longitudinal axes of valve passages 50B, 50C and 50D are each disposed at an angle with the longitudinal axis of sleeve 12 in the first rotational position for valve body 36. It should be appreciated that, depending on the number and/or size of the valve passages, all of the valve passages can be disposed at an angle with lumen 20 when the valve body is in the first rotational position such that no valve passage is axially aligned with the lumen of the sleeve when the valve passage defining section is moved into the sleeve lumen as explained below.

The valve body 36 is movable longitudinally or axially in cavity 28 in the direction of sleeve 12 from the extended position to a depressed position thusly compressing spring 38. Movement of valve body 36 inwardly so that the peripheral edge 72 of the lumen blocking section 46 abuts the end cap 30 causes the valve passage defining section 44 to be aligned with the longitudinal axis of sleeve 12 such that the valve passage defining section 44 is disposed in the lumen 20. Since valve passage 50A is disposed parallel with the longitudinal axis of sleeve 12 with the valve body 36 in the first rotational and the extended positions, movement of valve body 36 longitudinally, inwardly to the depressed position causes valve passage 50A to be aligned with the sleeve longitudinal axis. Accordingly, valve 14 will be in an open position allowing an instrument to be introduced through valve passage 50A and lumen 20 to extend through the valve body 36. It should be appreciated, however, that where all of the valve passages are disposed non-parallel or at an angle with the lumen 20 with the valve body in the first rotational and the extended positions, no valve passage will be axially aligned with lumen 20 when the valve body is moved longitudinally to the depressed position such that the valve will not be in the open position. Accordingly, the valve body must be rotated from the initial or first rotational position to a further, second or different rotational position to axially align a selected valve passage with the lumen 20 as described hereinbelow for alignment of one of valve passages 50B, 50C or 50D with lumen 20.

In order to align a selected valve passage 50B, 50C or 50D with lumen 20, valve body 36 is rotated about its longitudinal axis, which is transverse or perpendicular to the longitudinal axis of sleeve 12, from the first rotational position to a second rotational position wherein the selected valve passage is axially aligned with lumen 20. For example, in order to align valve passage 50B with lumen 20, valve body 36 must be rotated 45° clockwise from the first rotational position to a second rotational position to axially align passage 50B with lumen 20; and, with the valve body 36 in the depressed position and in the second rotational position, the valve 14 will be in a second open position with valve passage 50B axially aligned with lumen 20 to receive an instrument therethrough. Rotation of valve body 36 from the first rotational position to a second rotational position causes spring 38 to be coiled or wound; and, upon release of the valve body 36, the spring 38 automatically returns the valve body to the first rotational position. As shown in FIG. 1, endoscopic portal 10 can include a port 68 in fluid communication with the lumen 20 for supplying fluids, such as insufflation gas, to the body cavity through sleeve 12. Port 68 includes a valve 70 for selectively controlling the flow of fluid through the lumen 20 of sleeve 12.

Figure 5:
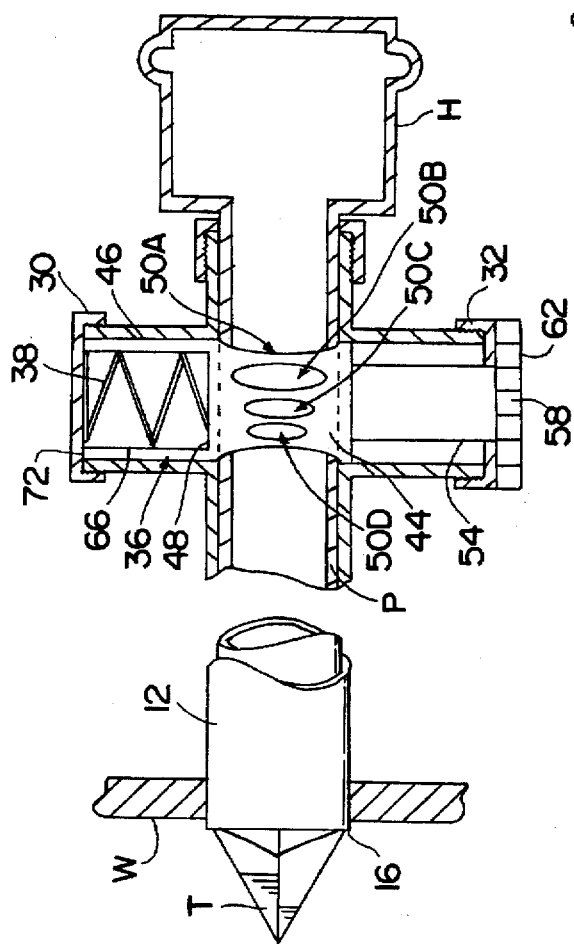
FIG. 5 is a broken, side sectional view of the endoscopic portal showing the valve in an open position to receive an instrument therethrough.

Prior to use, valve 14 is in the normal closed position shown in FIG. 1 with valve body 36 in the first rotational position and in the extended position. Lumen blocking section 46 is disposed within lumen 20 in alignment with the longitudinal axis of sleeve 12 such that wall 66 extends across lumen 20 to block lumen 20 and close off and seal sleeve 12. When a penetrating member is utilized to position sleeve 12 to extend through a wall of a body cavity, a penetrating member is optimally selected in accordance with the procedure to be performed and the type of anatomical cavity to be penetrated. For example, in FIG. 5, a 10 mm diameter penetrating member P has been selected to penetrate cavity wall W. In order to pass the penetrating member P through sleeve 12, knob 58 is grasped and used to manually move the valve body longitudinally or axially inwardly toward sleeve 12 in the direction transverse or perpendicular to the sleeve longitudinal axis against the bias of spring 38. Once peripheral edge 72 of lumen blocking section 46 engages the end cap 30 to serve as a positive stop limiting movement of valve body 36 inwardly, the valve body 36 will be in the depressed position while remaining in the first rotational position. In the case of valve 14, valve 14 will be in an open position with the lumen blocking section 46 disposed in end member 24 and the valve passage defining section 44 disposed in lumen 20 with the valve passage 50A axially aligned with the sleeve longitudinal axis. The indicia 64 for valve passage 50A will be in line with the sleeve longitudinal axis to visually indicate alignment of valve passage 50A therewith. Accordingly, the valve passage 50A corresponding in size to the size of penetrating member P will be axially aligned with the lumen 20 allowing the penetrating member P to be passed through the valve body 36 and the lumen 20 via the aligned valve passage 50A. The penetrating member P is manipulated via a hub H at a proximal end thereof. As shown in FIG. 5, with valve 14 in the open position, penetrating member P is passed through valve passage 50A corresponding in size to the diameter of the penetrating member P such that a distal tip T of the penetrating member P protrudes beyond the distal end 16 of sleeve 12 for use in penetrating the anatomical wall W. When the knob 58 is released, the valve 14 is prevented from returning to the closed position due to the presence of the penetrating member in valve passage 50A. Since the penetrating member P extends through the valve passage 50A having a diameter that is the same as the diameter of the penetrating member, the penetrating member P is in sealing relation with the valve 14 and fluid flow or leakage through the endoscopic portal 10 is prevented. Penetration through the cavity wall W by the penetrating member P causes the sleeve 12 to follow the penetrating member P through the cavity wall W; and, once the distal end 16 of sleeve 12 is disposed in the body cavity, the penetrating member P can be slidably withdrawn from the sleeve 12 leaving the sleeve 12 in place to provide a passage through the cavity wall W for the introduction of instruments. Withdrawal of the penetrating member P from the sleeve 12 causes the valve 14 to return automatically to the closed position due to the valve body 36 being biased axially by spring 38. Various fluids such as insufflation gas can be introduced in the body cavity through the port 68, and such fluids will be prevented from leaking when the valve 14 is in the closed position and when instruments extend through the valve assembly in sealing relation therewith.

In order to introduce a different size instrument through endoscopic portal 10 in sealing relation, a valve passage 50 is selected corresponding to the size of the instrument to be introduced. As shown in FIG. 6, valve passage 50C has been selected for axial alignment with lumen 20 to receive a 5 mm diameter needle instrument I. Knob 58 is manually grasped and utilized to move valve body 36 longitudinally or axially inwardly in the direction transverse to the sleeve longitudinal axis from the extended position to the depressed position. Prior to, subsequent to or simultaneously with movement of valve body 36 to the depressed position, knob 58 is used to manually rotate the valve body about its longitudinal axis from the first rotational position to a second rotational position wherein the indicia 64 for valve passage 50C are in line with the longitudinal axis of sleeve 20. As shown in FIG. 6, valve body 36 is rotated clockwise 90° from the first rotational position to the second rotational position to axially align valve passage 50C with the lumen 20. The valve 14 is then in a second open position with valve body 36 in the depressed position and in the second rotational position, and the instrument I is passed through the valve 14 and lumen 20 to be sealingly received in valve passage 50C. The presence of instrument I in the valve body prevents the valve body from returning to the extended position and the first rotational position when the knob 58 is released. Upon withdrawal of instrument I manually from valve 14, the valve body 36 automatically returns to the normal closed position due to the axial bias of spring 38 returning the valve body to the extended position and the rotational bias of spring 38 returning the valve body to the initial rotational position.

It should be appreciated that the valve body can be easily removed and replaced with a different valve body allowing the endoscopic portal to be used with various diverse valve bodies having different sizes or ranges of sizes of valve passages. Accordingly, a valve body can be optimally selected for use in a procedure in accordance with the sizes of instruments to be introduced such that the valve body selected has valve passages corresponding in size to the sizes of all of the instruments to be used.

From the above, it will be appreciated that the endoscopic portal of the present invention can be used for engaging medical instruments of various sizes in sealing relation to prevent fluid flow therethrough while allowing the medical instruments to be introduced into an anatomical cavity and removed in succession during a procedure. The multiluminal trumpet valve of the present invention can be used in combination with conventional valves for endoscopic portals and/or resilient seals and the like to provide added protection against leakage; however, the multiluminal trumpet valve is particularly advantageous when used alone in order to reduce the overall size of the endoscopic portal. The components of the endoscopic portal can be made of any suitable medical grade materials to permit sterilization for reuse or for single patient use and can be made of multiple parts of various configurations and materials to reduce costs. The valve body can have various configurations and can be made of separate parts or as a single part integrally, unitarily formed. The bias member for returning the valve body to the closed position can include any resilient member or mechanism, including coil springs, leaf springs, elastic cords, bends, magnets and elastic membranes. The valve body can be automatically or manually locked in one or more predetermined positions aligning a selected valve passage with the lumen by, for example, utilizing detents that engage the valve body and are released either manually or in response to withdrawal of the instrument from the sleeve. The sizes of the valve passages can be selected to cover a wide range of sizes of commonly used instruments. Valve bodies can be designed for particular operative procedures such that a single valve body provides valve passages corresponding in size to the sizes of all of the instruments normally used in a particular procedure.

In as much as the present invention is subject to many variations, modifications and changes in detail, it is intended that all subject matter discussed above or shown in the accompanying drawings be interpreted as illustrative only and not be taken in a limiting sense.

What is claimed:

1. An endoscopic portal for establishing communication with a body cavity for the introduction of instruments through the endoscopic portal comprising a sleeve for providing a passage through a cavity wall and having a distal end for being disposed in a body cavity, a proximal end for being disposed externally of the body cavity, a longitudinal axis and a lumen between said distal and proximal ends; and a valve carried by said sleeve and including a valve axis transverse to said longitudinal axis, a valve body and a bias member biasing said valve body axially for axial movement relative to said sleeve in a direction transverse to said longitudinal axis and biasing said valve body rotationally for rotational movement relative to said sleeve about said valve axis, said valve body including a blocking portion and a valve passage defining portion having a plurality of valve passages therethrough each having a different cross sectional size, said valve body being biased by said bias member to a closed position wherein said blocking portion is disposed in said lumen and said valve passage defining portion is disposed externally of said lumen, said valve body being movable axially from said closed position in said direction transverse to said longitudinal axis and rotationally about said valve axis to selectively align one of said valve passages axially with said lumen whereby an instrument having a cross sectional size corresponding to said cross sectional size of said one valve passage can be introduced through said one valve passage and said lumen to pass through said valve body in sealing relation therewith.

2. An endoscopic portal as recited in claim 1 wherein said valve is disposed between said distal and proximal ends of said sleeve.

3. An endoscopic portal for establishing communication with a body cavity for the introduction of instruments through the endoscopic portal comprising a sleeve for providing a passage through a cavity wall and having a distal end for being disposed in a body cavity, a proximal end for being disposed externally of the body cavity, a longitudinal axis and a lumen between said distal and proximal ends; and a valve carried by said sleeve and including a valve body mounted to said sleeve for movement in a direction transverse to said longitudinal axis, said valve body including a blocking portion and a valve passage defining portion having a plurality of valve passages therethrough each having a different cross sectional size, said valve body including a cylindrical member having a hollow section defining said blocking portion, a solid section defining said valve passage defining portion and a plurality of diametric passages formed in said solid section defining said valve passages, said valve body being biased to a closed position wherein said blocking portion is disposed in said lumen and said valve passage defining portion is disposed externally of said lumen, said valve body being movable from said closed position in said direction transverse to said axis to selectively align one of said valve passages axially with said lumen whereby an instrument having a cross sectional size corresponding to said cross sectional size of said one valve passage can be introduced through said one valve passage and said lumen to pass through said valve body in sealing relation therewith.

4. An endoscopic portal as recited in claim 3 wherein said valve body further includes a handle coupled with said cylindrical member for manually moving said valve body from said closed position to selectively align one of said valve passages axially with said lumen.

5. An endoscopic portal as recited in claim 4 wherein said handle includes a shaft protruding from said valve body and a knob carried by said shaft.

6. An endoscopic portal as recited in claim 5 wherein said valve further includes a spring biasing said valve body to said closed position.

7. An endoscopic portal as recited in claim 6 wherein said sleeve includes a pair of hollow end members extending transversely from said sleeve and communicating with said lumen, said end members having a common longitudinal axis disposed perpendicular to said longitudinal axis of said sleeve, said end members defining a cavity in which said valve is received.

8. An endoscopic portal as recited in claim 7 wherein said end members extend transversely from said sleeve to terminate at outer ends and further including an end cap disposed on each of said outer ends, said spring being disposed between said valve body and one of said end caps.

9. An endoscopic portal as recited in claim 8 wherein said blocking portion has a recess therein and said spring is disposed in said recess.

10. An endoscopic portal for establishing communication with a body cavity for the introduction of instruments through the endoscopic portal comprising a sleeve for providing a passage through a cavity wall and having a distal end for being disposed in a body cavity, a proximal end for being disposed externally of the body cavity, a lumen between said distal and proximal ends and a longitudinal axis; and a valve carried by said sleeve and including a valve body having a longitudinal axis, a blocking portion and a valve passage defining portion having a plurality of valve passages therethrough each having a different cross sectional size, said valve body being biased axially relative to said sleeve to an extended position wherein said valve passage defining portion protrudes laterally from said sleeve and said blocking portion is disposed in said lumen to block communication therewith, said valve body being biased rotationally relative to said sleeve to a first rotational position wherein at least one of said valve passages is disposed at an angle with said longitudinal axis of said sleeve, said valve body being movable axially against said axial bias to position said valve passage defining portion in said lumen and being rotatable about said longitudinal axis of said valve body against said rotational bias to align said one valve passage axially with said lumen to provide a passage through said valve body for receiving an instrument through said one valve passage in sealing relation.

11. An endoscopic portal as recited in claim 10 wherein said valve includes a bias member biasing said valve body axially and rotationally.

12. An endoscopic portal as recited in claim 11 and further including a housing receiving said valve and wherein said bias member includes a helical coil spring connected to said housing and said valve body.

13. An endoscopic portal as recited in claim 12 wherein said housing is disposed between said distal and proximal ends of said sleeve.

14. An endoscopic portal as recited in claim 13 wherein said valve passages have longitudinal axes disposed perpendicular to said longitudinal axis of said valve body.

15. An endoscopic portal as recited in claim 14 wherein said valve body is rotatable about said longitudinal axis of said valve body to align said one valve passage axially with said lumen.

16. An endoscopic portal for establishing communication with a body cavity for the introduction of instruments through the endoscopic portal comprising a sleeve for providing a passage through a cavity wall and having a distal end for being disposed in a body cavity, a proximal end for being disposed externally of the body cavity, a lumen between said distal and proximal ends and a longitudinal axis; and a valve carried by said sleeve and including a cylindrical valve body extending in a transverse direction across said lumen and having a plurality of intersecting diametric valve passages therethrough of different cross sectional sizes, said valve body being biased to a closed position wherein said valve body blocks communication through said lumen and said valve passages are not disposed within said lumen, said valve body being movable axially from said closed position in said transverse direction to position said valve passages within said lumen, said valve body being rotatable about an axis transverse to said longitudinal axis of said sleeve to align a selected one of said valve passages axially with said lumen such that an instrument having a size corresponding to said cross sectional size of said selected valve passage can be introduced therethrough to extend through said valve in sealing relation.

17. An endoscopic portal as recited in claim 16 wherein said valve body has four valve passages disposed at 45° spaced locations.

18. An endoscopic portal as recited in claim 16 wherein said valve includes indicia for visually indicating the location and size of said valve passages.

19. An endoscopic portal as recited in claim 18 wherein said valve includes a handle for manually moving said valve body axially and rotationally and said indicia is disposed on said handle.

20. An endoscopic portal as recited in claim 19 and further including a removable end cap at said proximal end of said sleeve and having an opening therein aligned with said lumen and corresponding in size to the cross sectional size of the instrument.

* * * * *